United States Patent
Osucha et al.

(10) Patent No.: US 7,253,414 B2
(45) Date of Patent: Aug. 7, 2007

(54) MULTI-ENERGY GAMMA ATTENUATION FOR REAL TIME CONTINUOUS MEASUREMENT OF BULK MATERIAL

(75) Inventors: Peter M. Osucha, Knoxville, TN (US); David K. Swindell, Knoxville, TN (US); Jack R. Lee, Lenoir City, TN (US)

(73) Assignee: Energy Technologies, Inc., Knoxville, TN (US)

( * ) Notice: Subject to any disclaimer, the term of this patent is extended or adjusted under 35 U.S.C. 154(b) by 191 days.

(21) Appl. No.: 10/875,907

(22) Filed: Jun. 24, 2004

(65) Prior Publication Data

US 2004/0262524 A1    Dec. 30, 2004

Related U.S. Application Data

(60) Provisional application No. 60/482,039, filed on Jun. 24, 2003.

(51) Int. Cl.
*G01N 23/222* (2006.01)
*G01F 23/00* (2006.01)
*G01N 23/00* (2006.01)

(52) U.S. Cl. ............... 250/358.1; 250/359.1; 250/390.04

(58) Field of Classification Search ............ 250/358.1, 250/359.1, 390.04, 393, 363.01; 702/2, 8, 702/26, 28
See application file for complete search history.

(56) References Cited

U.S. PATENT DOCUMENTS

| | | | |
|---|---|---|---|
| 4,442,701 A * | 4/1984 | Cowherd et al. | 73/32 R |
| 4,582,992 A | 4/1986 | Atwell et al. | |
| 4,682,043 A * | 7/1987 | Marshall | 250/358.1 |
| 5,825,030 A * | 10/1998 | Hurwitz et al. | 250/358.1 |
| 6,362,477 B1 | 3/2002 | Sowerby et al. | |
| 6,624,425 B2 * | 9/2003 | Nisius et al. | 250/393 |
| 6,740,887 B1 * | 5/2004 | Parvin et al. | 250/393 |
| 7,006,919 B2 * | 2/2006 | Osucha et al. | 702/2 |
| 2003/0225531 A1 * | 12/2003 | Lingren et al. | 702/23 |

* cited by examiner

*Primary Examiner*—David Porta
*Assistant Examiner*—Faye Boosalis
(74) *Attorney, Agent, or Firm*—Pitts & Brittian, PC

(57) ABSTRACT

Methods and apparatus for continuous real-time measurement of bulk material using gamma irradiation. A multi-energy gamma attenuation device monitors bulk material flow and produces a spectrum that is compared to a baseline spectrum to produce a relative weight/impurity/component ratio. A sample analysis, in combination with measurement of the relative weight/impurity/component ratio of the sample, allows for determination of the coefficients for determining the absolute weight/impurity/component values of the bulk material.

43 Claims, 6 Drawing Sheets

MULTI-ENERGY GAMMA ATTENUATION FOR REAL TIME CONTINUOUS MEASUREMENT OF BULK MATERIAL

CROSS-REFERENCE TO RELATED APPLICATIONS

This application claims priority from Provisional Application Ser. No. 60/482,039, filed Jun. 24, 2003.

STATEMENT REGARDING FEDERALLY SPONSORED RESEARCH OR DEVELOPMENT

Not Applicable

BACKGROUND OF THE INVENTION

1. Field of Invention

The present invention relates to the use of radiation response measurements for determining the quality and quantity of bulk material in an on-line process. More particularly, this invention pertains to Multi-energy Gamma Attenuation (MGA).

2. Description of the Related Art

Several technologies exist to determine the composition of bulk materials. One that is especially important to the present invention is Dual-energy Gamma Attenuation (DGA) analysis.

Dual-energy Gamma Attenuation (DGA) based sensors have been used for many years. A DGA device operates on the premise that analyzed material will attenuate different energy gamma rays in fixed repeatable ways. A DGA device consists of a gamma energy source arrangement consisting of dual energy gamma emitters. The gamma emitters are chosen in such a way that the material to be analyzed will attenuate the different energy gamma rays in ways that are conducive to measuring one or more specific properties of the material being measured. The DGA technique relies on the fact that material is composed of constituents with a range of atomic numbers and that a distinction between the constituents is advantageous in processing. The attenuation of higher-energy gamma energy is relatively insensitive to the material's atomic number, but the attenuation of lower-energy gamma energy is very sensitive to the material's atomic number. These different attenuation characteristics can strongly differentiate between high and low atomic number material constituents. Two sources are used in DGA analysis: a low-energy source (typically at 60 KeV) and a high-energy source (typically at 662 KeV). The energy attenuation from the two sources resulting from transmission through the analyzed material can then be combined to distinguish between materials of different composition. This technique does not allow for identification of specific elements, but instead only characteristics of the composition. One such application of DGA technology uses gamma ray sources to interrogate coal, with the assumption that the material that coal is composed of will attenuate the differing energy gamma rays to produce a measurement that is conducive to determining coal ash content and density. For other mineral compositions, this technique is used to distinguish between the desired mineral and the undesirable overburden or interburden.

The DGA analysis technique involves bombarding a bulk material with gamma rays from two gamma ray emitters of sufficiently different energies. The gamma rays interact with the bulk material resulting in the attenuation of the number of gamma rays transmitted through the bulk material. The gamma rays are typically detected by a scintillation crystal (typically NaI) monitoring the two energy levels of the sources. The sum of these released gamma rays at these specific energies is referred to as an energy spectrum. The technology relies on the fact that elements with different atomic numbers attenuate gamma rays at specific energies in different ways. Thus, for low-energy gamma rays (i.e., those generated by a low energy gamma emitter such as Am-241), the attenuation of gamma rays is largely dependent on the atomic number of the atoms/elements present in the bulk material. For high-energy gamma rays (i.e., those generated by a high-energy gamma emitter such as Cs-137), attenuation is largely independent of the atoms/elements in the bulk material. Analysis of the energy spectrum leads to a determination of the bulk elemental composition of the bulk material.

BRIEF SUMMARY OF THE INVENTION

The present invention provides methods and apparatus for the measurement of bulk material quality and content using multi-energy gamma attenuation (MGA). In one embodiment the method consists of the use of several gamma emitters at various energies to determine the bulk material quality and content. The apparatus is a multiple-energy (three or more sources) gamma attenuation analyzer including a shielded source enclosure, a detector assembly, and a structural support framework defining an analysis zone in which the bulk material to be analyzed passes. The apparatus includes an MGA device to determine the absolute material density and content, and a computing/processing system for combining the resultant sensor data into quantities representative of the material quality.

In one embodiment, gamma sources emitting gamma radiation of at least three different energy levels are monitored by a detector responsive to the energy range encompassing the sources energy levels. The detectors produce spectrums of the detected energy range. An empty spectrum, measured with no bulk material in the detection path, is combined with a material spectrum, measured with the gamma radiation passing through the bulk material, to produce an attenuation gamma spectrum, which is compared to a gamma attenuation library. The gamma attenuation library includes mass attenuation coefficients determined for the pure elements or compounds expected to be in the bulk material. The full spectrum comparison with the library results in relative weight/impurity/component ratios. These relative ratio values provide the basis for determining the absolute weight/impurity/component values. This determination is made with equations having coefficients determined by comparing laboratory analysis of samples with the measured spectra of the samples.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A measurement system for continuous real-time measurement of bulk material is disclosed. The measurement system is shown as item 10 on the figures. The measurement system 10 is a multiple-energy (three or more sources) gamma attenuation analyzer including a shielded source enclosure, a detector assembly, and a structural support framework defining an analysis zone in which the bulk material 114 to be analyzed passes. The purpose of the shielded source enclosure is to provide radiation shielding for personnel. The detector houses the detection components and provides shielding from gamma energy produced from other sources. The signals detected provide a measurement of multiple characteristics and specific elemental content of the bulk material as it passes through the analysis zone.

Figure 1:
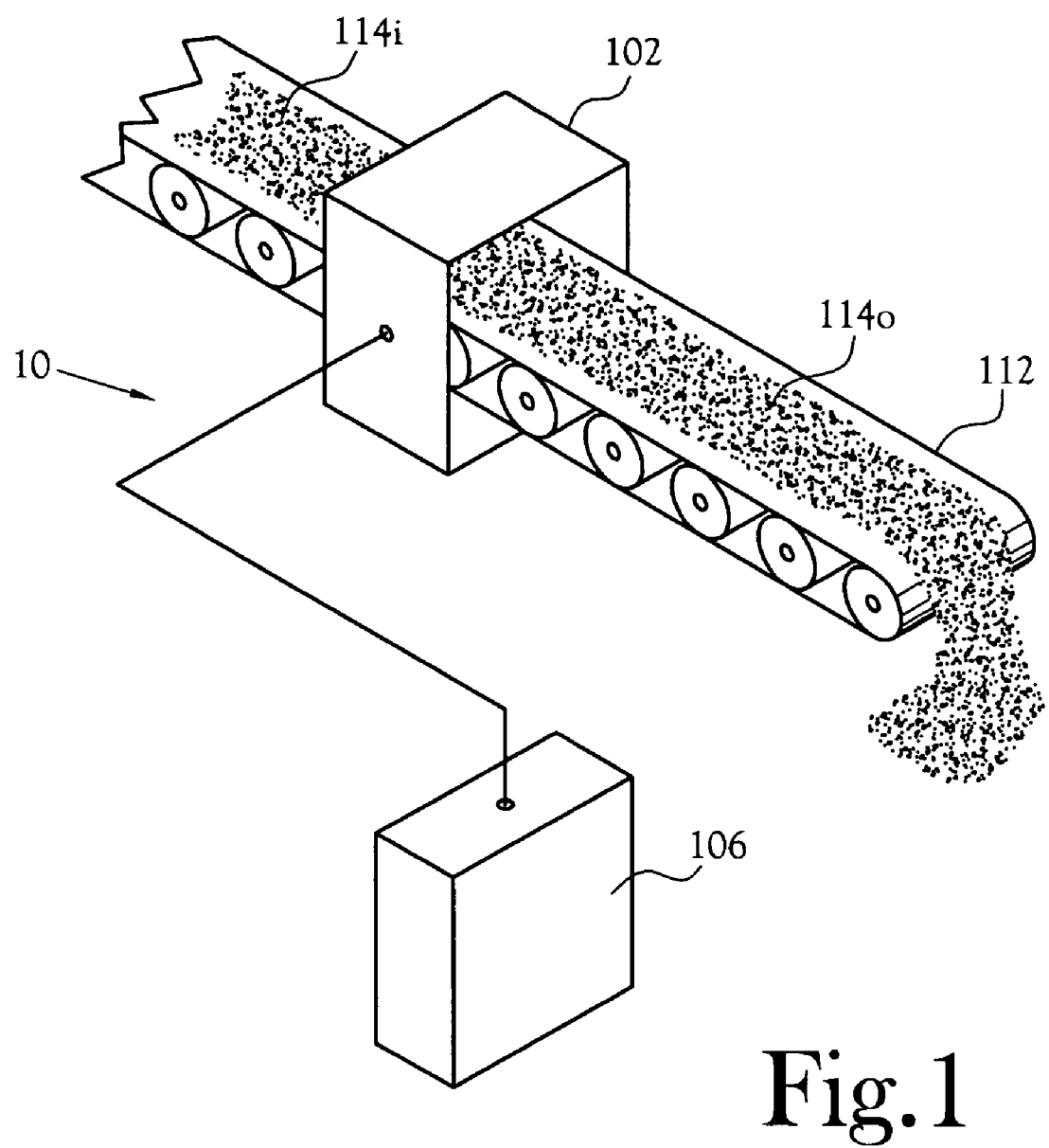
FIG. 1 is a pictorial view of one embodiment of the apparatus.

FIG. 1 illustrates one embodiment of the measurement system 10 as it is used with a conveyor 112 carrying bulk material 114$i$ into and bulk material 114$o$ out of a multi-energy gamma attenuation unit (MGA) 102. The MGA device 102 communicates with a processor 106. Those skilled in the art will recognize that the bulk material 114 can be monitored by the MGA device 102 in various manners, including the illustrated conveyor and a drop chute, without departing from the spirit and scope of the present invention.

Figure 2:
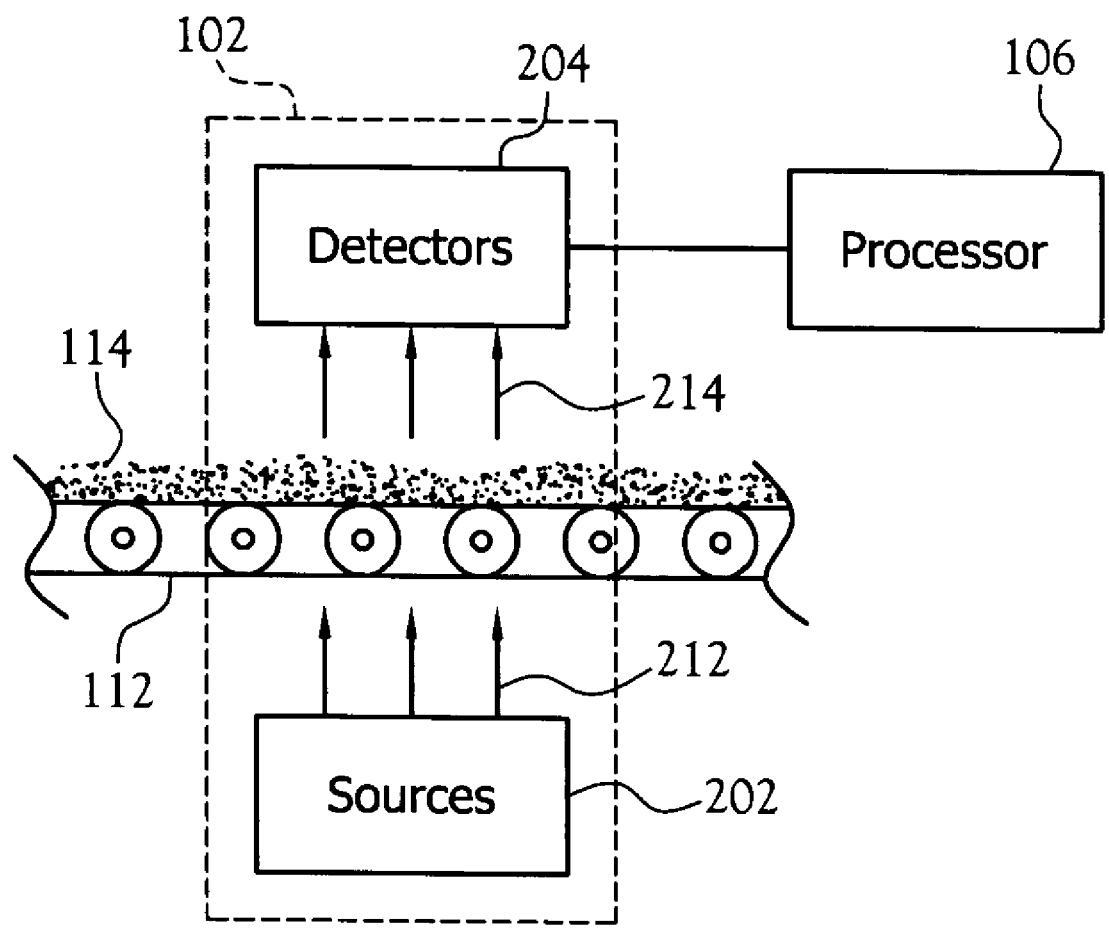
FIG. 2 is a block diagram of one embodiment of the apparatus.

FIG. 2 illustrates a block diagram showing the measurement system 10. In the illustrated embodiment, sources 202 are located under a conveyor 112 carrying the bulk material 114. The sources 202 direct gamma radiation 212 of various energies through the bulk material 114. After passing through the bulk material 114, attenuated gamma radiation 214 is received by the detectors 204. The output of the detectors 204 is directed to a processor 106, which receives a data stream corresponding to the detected attenuated gamma radiation 214. The sources 202 emit gamma radiation 212 at three or more energy levels. In one embodiment, each energy level is selected based on its attenuation by the expected bulk material 114 to be measured. In another embodiment, the energy levels are selected to provide a broad coverage over an energy range. See FIG. 6. The detectors 204 are responsive to each energy level and measure the amount of attenuation of the source gamma radiation 212 after the source gamma radiation 212 passes through the bulk material 114. Although the illustrated embodiment shows the bulk material 114 on a conveyor 112 with the sources 202 under the material 114, the present invention is not limited to that configuration. The sources 202 are located opposite the detectors 204 with the bulk material 114 between the sources 202 and the detectors 204.

As used herein, the processor 106 should be broadly construed to mean any computer or component thereof that executes software. The processor 106 includes a memory medium that stores software, a processing unit that executes the software, and input/output (I/O) units for communicating with external devices. Those skilled in the art will recognize that the memory medium associated with the processor 106 can be either internal or external to the processing unit of the processor without departing from the scope and spirit of the present invention. Further, in one embodiment, the processor 106 communicates with the MGA device 102 via a network connection.

In one embodiment the processor 106 is a general purpose computer, in another embodiment, it is a specialized device for implementing the functions of the invention. Those skilled in the art will recognize that the processor 106 includes an input component, an output component, a storage component, and a processing component. The input component receives input from external devices, such as the MGA device 102, and a terminal device for operator input. The output component sends output to external devices, such as a printer, a display device, or another computer system or network. The storage component stores data and program code. In one embodiment, the storage component includes random access memory. In another embodiment, the storage component includes non-volatile memory, such as floppy disks, hard disks, and writeable optical disks. The processing component executes the instructions included in the software and routines.

Figure 3:
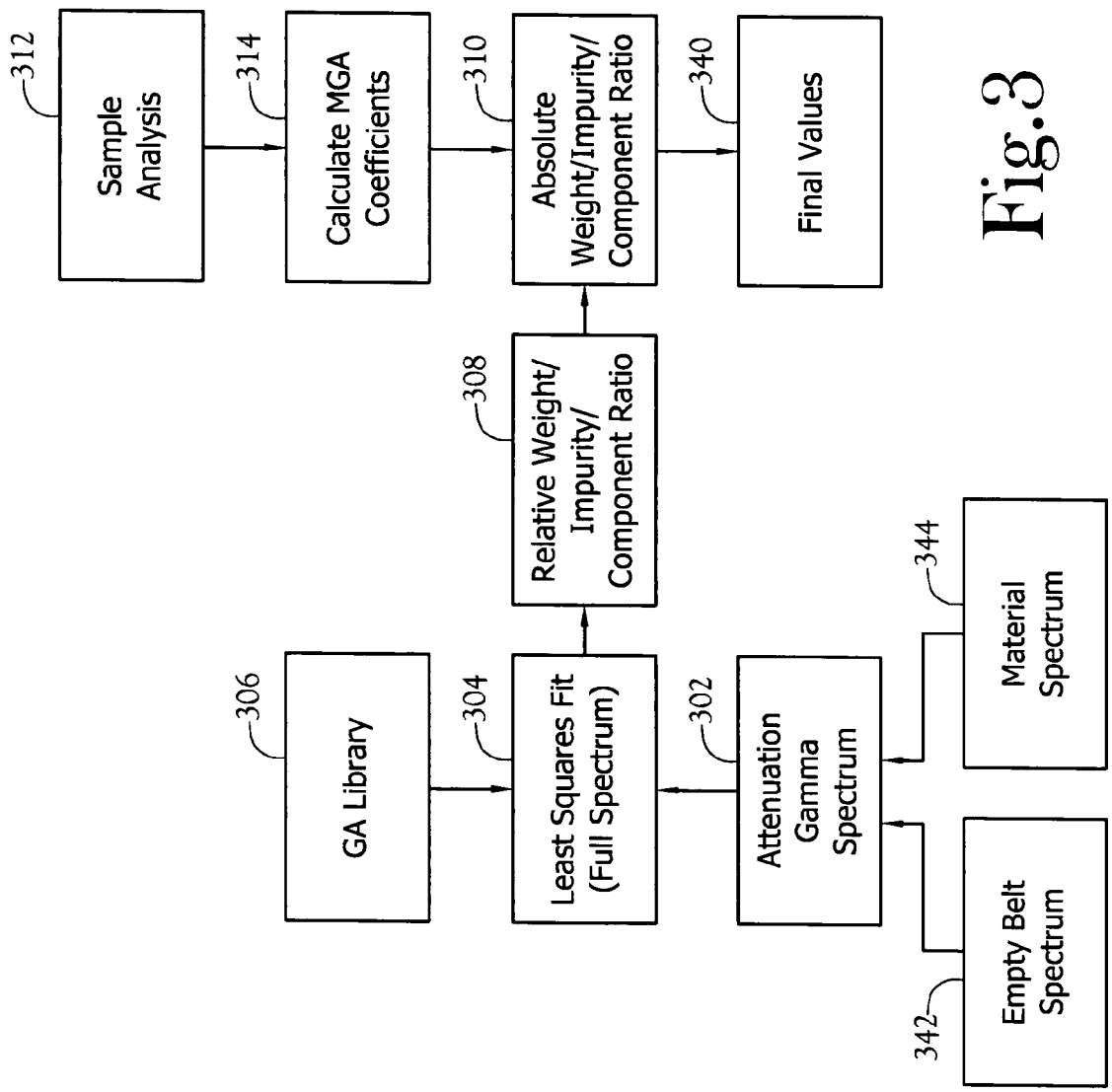
FIG. 3 is a flow diagram of one embodiment of the apparatus.
Figure 4:
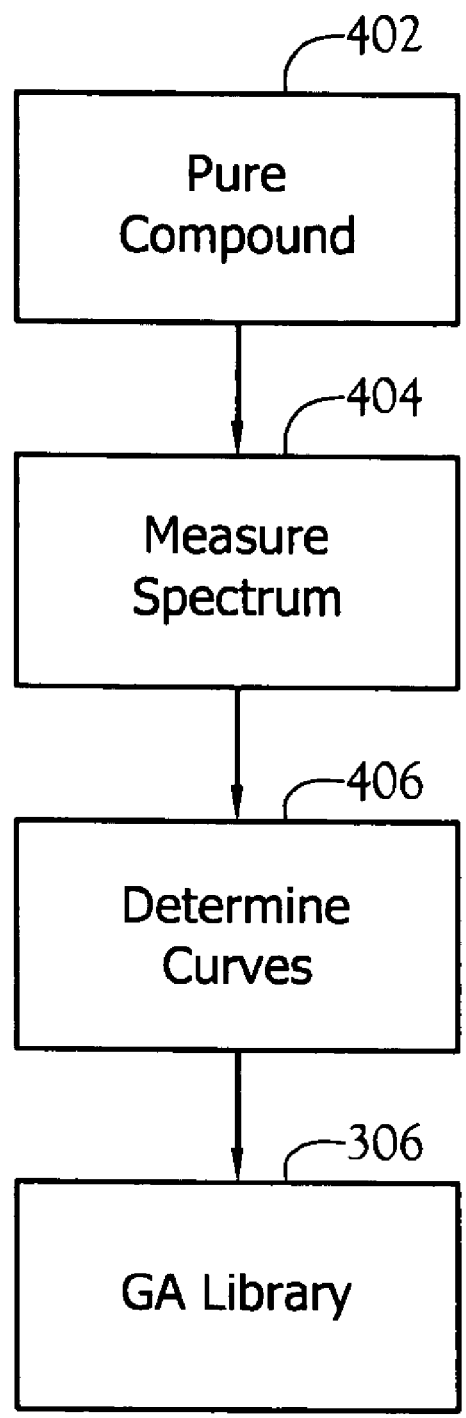
FIG. 4 is a block diagram of one embodiment of building a gamma attenuation library.

FIG. 3 illustrates a block diagram of one embodiment of the measurement system 10. The bulk material transport mechanism (conveyor in FIGS. 1 and 3) 112 moves the bulk material 114 through the MGA device 102. Gamma rays 212 emitted by the sources 202 in the MGA device 102 are transmitted through the bulk material 114. These gamma rays interact with the bulk material 114 and are monitored by the detectors 204 of the MGA device 102, in which the detected energy is converted into electronic signals. The electronic signals are analyzed by the processor 106 and compared with similar signals from a material free interrogation zone to give an indication of bulk material density and elemental content.

Figure 5:
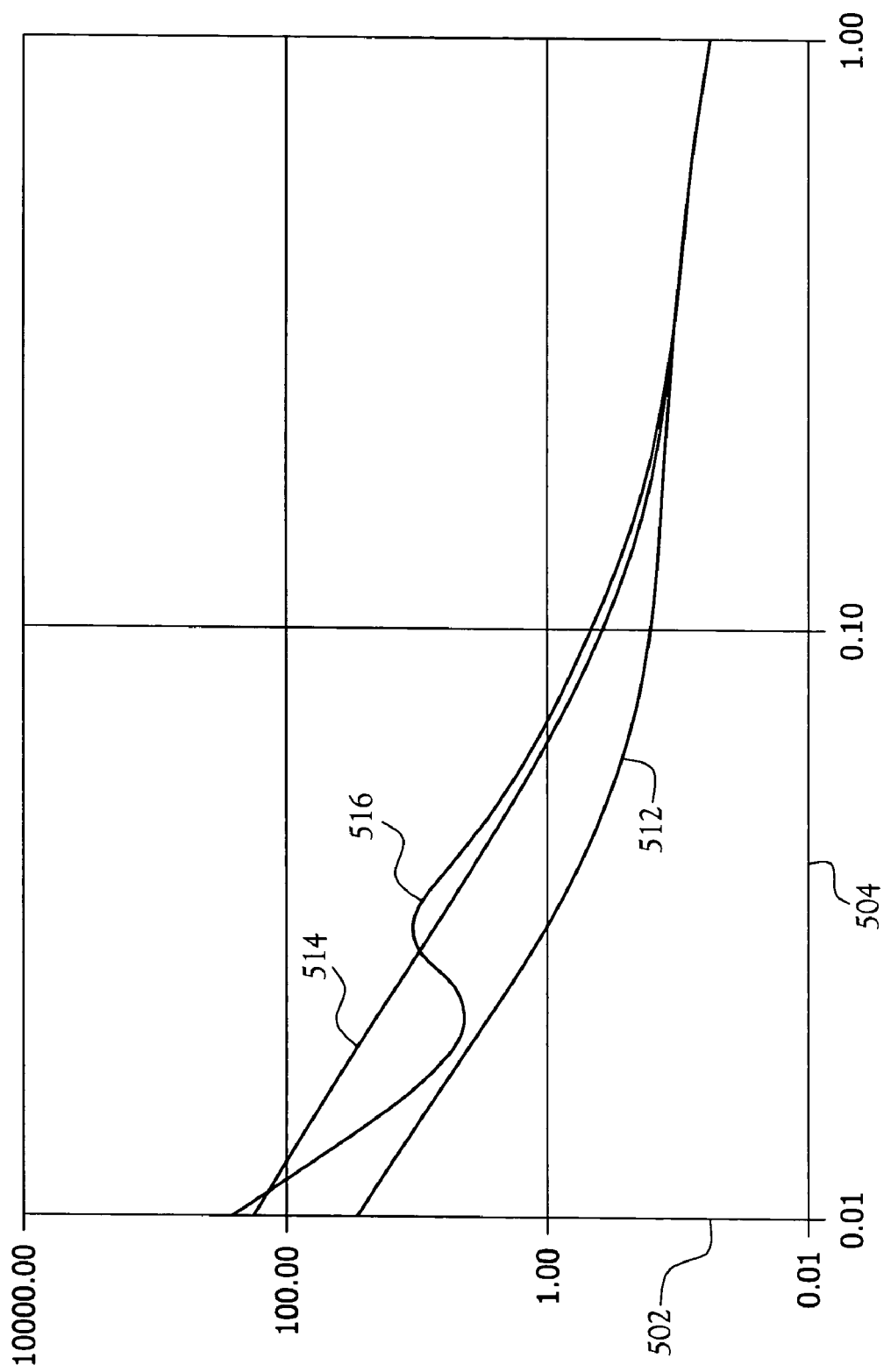
FIG. 5 is a graph illustrating mass attenuation coefficients of several elements.

To perform the MGA measurement, gamma rays 212 emitted by the MGA sources 202 are collected for a particular length of time to create an empty belt, or baseline, gamma attenuation (GA) spectrum 342. The generated spectrum is representative of the measurements obtained with no bulk material 114 being irradiated. Bulk material 114 is then introduced and a material spectrum 344 is obtained. These two spectrums 342, 344 are combined to produce an attenuation gamma spectrum 302 that is representative of the attenuation spectrum attributed to only the bulk material. In the illustrated embodiment, the attenuation gamma spectrum 302 is compared to the gamma attenuation library 306 by performing a least squares fit of the full spectrum 304 of the measured gamma spectrum 302 with the baseline spectra in the gamma attenuation library 306. FIG. 5 illustrates a block diagram showing the steps for building the gamma attenuation library 306. The result of the least squares fit operation 304 is a relative measurement of the bulk material constituents, or a relative weight/impurity/component ratio 308. In one embodiment, constituents include silica, calcium, and sodium for coal as a bulk material 114. In another embodiment, the constituents include the basic elements, such as iron, copper, and carbon.

The absolute weight/impurity/component determination 310 is performed by applying certain equations to the relative weight/impurity/component ratio 308. In one embodiment, the determination of the absolute weight, the determination of the absolute impurity, and the determination of the absolute components 310 are based on the following equations:

$$\text{Weigh}_{abs} = f(\text{Weight}_{rel})$$

$$\text{Impurity}_{abs} = f(\text{Impurity}_{rel})$$

$$\text{Component}_{abs} = f(\text{Component}_{rel})$$

In other words, the absolute weight (Weight$_{abs}$) is a function of the relative weight (Weight$_{rel}$), the absolute impurity (Impurity$_{abs}$) is a function of the relative impurity (Impurity$_{rel}$), and the absolute component (Component$_{abs}$) is a function of the relative component (Component$_{rel}$). In one embodiment, these three equations are solved simultaneously to determine the absolute weight, impurity, and component levels. In one embodiment, the absolute weight, impurity, and component values are in units of percent weight.

The coefficients of these equations are determined by first performing a sample analysis 312 that includes testing samples of bulk material 114 for impurities with laboratory or other special equipment to determine the constituent or component concentrations. The sample analysis 312 also includes running the samples of bulk material 114 through the MGA device 102 to obtain measured relative weight/impurity/component ratios 308. By measuring the relative weight/impurity ratios of the bulk material 114 samples with known impurities, the various coefficients for the above polynomial equations used in determining absolute weight, impurity, and components are refined and adjusted in the step of calculating the MGA coefficients 314. The sample analysis 312 and the step of calculating the MGA coefficients 314 are performed, in one embodiment, as a calibration, which is repeated as necessary to ensure accurate results.

For example, with coal being the bulk material 114, at least two samples with a known ash content are measured by the MGA device 102. The coefficients of the polynomial equations used in determining absolute weight, impurity, and component are adjusted to curve-fit the equations with the relative weight/impurity ratio 308 measurements. After the MGA coefficients are determined 314, the absolute weight/impurity/component determination 310 of the bulk material 114 is made by applying each measured relative weight/impurity/component ratio 308 to the equations above. In one embodiment, the result 340 from the absolute weight/impurity/component determination 310 is an absolute weight, an absolute impurity, and an absolute component, in units of percent weight.

The absolute/impurity/component determination 310 relates the 'relative' measured values 308 to the absolute values 340. It should also be noted here that the higher energy attenuation information can be used as a relative indication of material density (and therefore, weight) of the bulk material. By knowing the weight of the measured bulk material, the impurity content, and the relative impurity compositions, absolute weight/impurity/component ratios 310 for the elemental content of the impurities are calculated.

The end result of the absolute weight/impurity/component determination 310 is to produce the absolute values 340 of the bulk material 114. The absolute values 340 include the weight and percent of the total for each component, including impurities. In another embodiment, the absolute values 340 include the weight and percent of the total for each element in the bulk material 114.

By accurately knowing the weight and impurity component of the bulk material 114 as well as the elemental content of the impurity component, mathematical models can be empirically created to provide additional or enhanced information on other components of the bulk material 114.

FIG. 5 illustrates a graph showing mass attenuation coefficients of several elements. The curves for each FIG. 5 is a graph illustrating mass attenuation coefficients of several elements. The Y-Axis 502 is a logarithmic scale of the attenuation coefficient. The X-axis 504 is a logarithmic scale of energy level. The three curves 512, 514, 514 represent the mass attenuation coefficients of three elements. In the illustrated example, aluminum 512, iron 514, and copper 516 are plotted.

Figure 6:
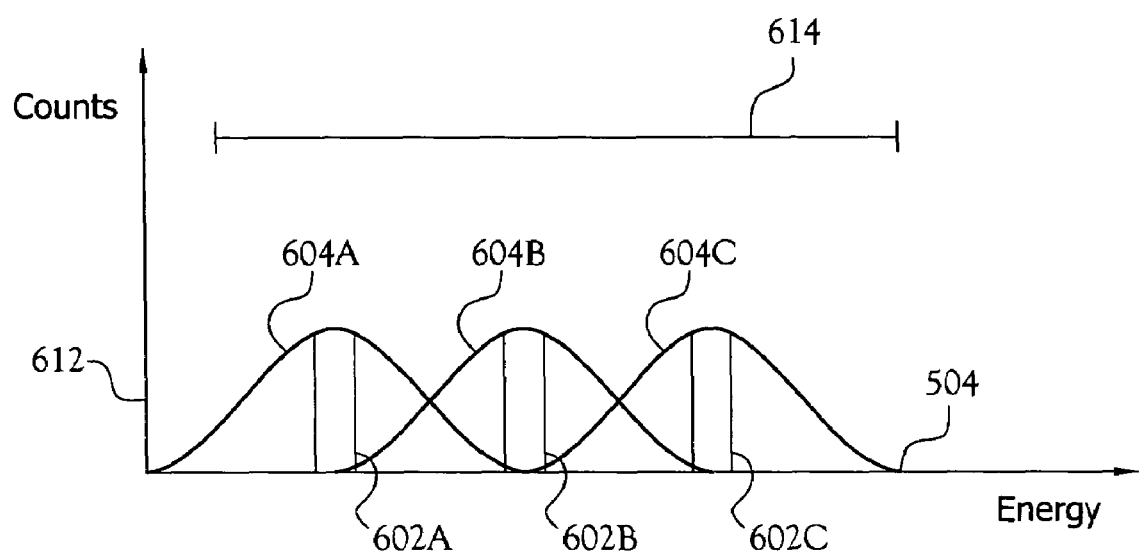
FIG. 6 is a graph illustrating the energy spectrum monitored by one embodiment of the present invention.

FIG. 6 is a graph illustrating the energy spectrum monitored by one embodiment of the present invention. The Y-Axis 612 represents the number of counts. The X-axis 504 represents the energy level. For the embodiment with three gamma sources 202, the first source 202 is a low energy source 602A that has a spread of emissions 604A at different energies. A second source 202 is a mid-energy source 602B that has a spread of emissions 604B at different energies. A third source 202 is a is a high-energy source 602B that has a spread of emissions 604B at different energies. The detectors 204 are responsive to energy levels over a continuous energy range 614. In the illustrated embodiment, the energy levels of the sources 202 are spaced such that the effective energy level evenly covers a broad range. Accordingly, with multiple energy sources 202 emitting gamma radiation over a wide energy range, sufficient information is available to determine the weight/impurity/component ratios 310.

In one embodiment, each of the functions identified above are performed by one or more software routines run by the processor 106. In another embodiment, one or more of the functions identified are performed by hardware and the remainder of the functions are performed by one or more software routines run by the processor 106.

The processor 106 executes software, or routines, for performing various functions. These routines can be discrete units of code or interrelated among themselves. Those skilled in the art will recognize that the various functions can be implemented as individual routines, or code snippets, or in various groupings without departing from the spirit and scope of the present invention. As used herein, software and routines are synonymous. However, in general, a routine refers to code that performs a specified function, whereas software is a more general term that may include more than one routine or perform more than one function. Those skilled in the art will recognize that it is possible to program a general-purpose computer or a specialized device to implement the invention.

The measurement system 10 includes several functions, both hardware and software. The system includes a function for obtaining a material spectrum 344 over a range of energies 614 that, in one embodiment, is performed by the sources 202 emitting gamma radiation 212 of at least three energy levels through the bulk material 114 to at least one detector 204. The system 10 includes a function for obtaining an empty spectrum 342 over a range of energies 614 that, in one embodiment, is performed by the sources 202 emitting gamma radiation 212 of at least three energy levels to at least one detector 204. For this function, the gamma radiation 212 does not pass through the bulk material. That is, the transport mechanism 112 is empty.

The system 10 includes a function for combining the material spectrum 344 with the empty spectrum 342 that, in one embodiment, is performed by the processor 106 executing software to produce an attenuation gamma spectrum 302.

The system 10 includes a function for determining at least one absolute value of a constituent the bulk material 114 that, in one embodiment, is performed by the processor 106 executing software to perform a least squares fit 304 with a gamma attenuation library 306 to determine relative measured values 308. In another embodiment, the relative measured values 308 are processed with calculated MGA coefficients 314 to determine the absolute values 310.

The accurate determination of the elemental content of coal is important to the industry. Coal is composed of combustible materials (i.e., carbon and hydrogen) and non-combustible impurity materials (i.e., aluminum, silicon, etc.) which are typically referred to as ash.

Those skilled in the art will recognize that the example description for use of the invention in the coal industry can easily be extrapolated to uses in the analysis of other bulk materials, for example, other mining industries (i.e., bauxite, copper mining, etc.) and processing industries (i.e., cement, phosphate, etc.) without departing from the spirit and scope of the present invention.

From the foregoing description, it will be recognized by those skilled in the art that a measurement system 10 has been provided. The measurement system 10 uses the outputs from a MGA device 102 to determine the absolute values 340 of the components of the bulk material 114. The outputs are combined, in one embodiment, by software executed by a processor 106 to produce an absolute impurity value and absolute analyte, or element, values for the bulk material. Because the MGA device 102 monitors the bulk material 114 as a process flow, the absolute values 340 produced reflect the process flow of bulk material 114.

The MGA technique has a distinct advantage over the DGA technique in that the atomic/elemental interaction with the gamma energy takes place at several energies that depend on the atomic number of the atom/element encountered. Therefore, knowing the relative attenuation of gamma rays at the energies of interest and the mathematical reduction of a measured energy spectra against the known relative attenuations results in a determination of the quality and content of the bulk material.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

The invention claimed is:

1. An apparatus for measuring an absolute value of at least one component of a bulk material, said apparatus comprising:
    a source of gamma radiation, said source emitting gamma radiation having at least three energy levels;
    at least one detector responsive to a continuous range of energy levels encompassing said at least three energy levels, said at least one detector and said source adapted for passing the bulk material between said at least one detector and said source;
    a first data set representing a measured gamma spectrum of the bulk material, said data set produced by said at least one detector;
    a processor in communication with said least one detector, said processor programmed to execute a process including:
    receiving said first data set,
    performing a least squares fit of said first data set with at least one library spectrum,
    determining a relative weight/impurity/component ratio of the bulk material from said first data set, and
    determining an absolute weight/impurity/component value from said relative weight/impurity/component ratio.

2. The apparatus of claim 1 wherein said process step of determining an absolute weight/impurity/component value from said relative weight/impurity/component ratio includes:
    receiving a sample data set from a sample analysis of at least one sample of the bulk material, said sample data set identifying at least one constituent of the bulk material, receiving a test data set including a sample relative weight/impurity/component ratio from a measurement of said at least one sample of the bulk material, and
    calculating at least one coefficient from said sample data set and said test data set.

3. The apparatus of claim 1 wherein said process step of determining an absolute weight/impurity/component value includes using at least one coefficient calculated by comparing a plurality of results from a test of at least one sample of the bulk material with known constituents and a measurement of a spectrum of said at least one sample.

4. The apparatus of claim 1 further including, before said step of performing said least squares fit, a process step of adjusting said first data set with a second data set representing a gamma spectrum measured with the bulk material not in a detection path of said at least one detector.

5. The apparatus of claim 1 wherein said at least one library spectrum includes at least one measured spectrum, each of said at least one measured spectrum representative of one of a pure element and a pure compound.

6. The apparatus of claim 1 wherein at least one of an absolute weight value, an absolute impurity value, and an at least one absolute analyte value of said absolute weight/impurity/component value is in units of weight percent.

7. An apparatus for measuring an absolute value of at least one component of a bulk material, said apparatus comprising:
    a source of gamma radiation, said source emitting gamma radiation having at least three energy levels;
    at least one detector responsive to a range of energy levels encompassing said at least three energy levels, said at least one detector and said source adapted for passing the bulk material between said at least one detector and said source;
    a first data set representing a measured gamma spectrum of the bulk material, said first data set produced by said at least one detector,
    a second data set representing a gamma spectrum measured with the bulk material not in a detection path of said at least one detector, said second data set produced by said at least one detector; and
    a processor in communication with said at least one detector, said processor programmed to execute a process including:
    receiving said first data set,
    receiving said second data set,
    combining said first data set and said second data set to produce an attenuation gamma spectrum;
    matching said attenuation gamma spectrum with a library containing at least one library spectrum,
    determining a set of relative values of the bulk material, and determining a set of absolute values of the bulk material based on at least one coefficient determined from a sample analysis.

8. The apparatus of claim 7 wherein said process step of matching includes performing a least squares fit of said attenuation gamma spectrum with a library containing at least one library spectrum.

9. The apparatus of claim 7 wherein said set of absolute values includes one of an absolute weight value, an absolute impurity value, and an absolute component value.

10. The apparatus of claim 7 wherein said at least one coefficient is determined by comparing a plurality of results from a test of at least one sample of the bulk material with a measurement of a spectrum of said at least one sample, said test identifying at least one constituent of the bulk material.

11. The apparatus of claim 7 wherein said library includes at least one curve of mass attenuation coefficients.

12. The apparatus of claim 7 wherein said library includes a measured spectrum of one of a pure element and a pure compound.

13. An apparatus for measuring an absolute value of at least one component of a bulk material, said apparatus comprising:
a source of gamma radiation, said source emitting gamma radiation having at least three energy levels;
at least one detector responsive to a range of energy levels encompassing said at least three energy levels, said at least one detector positioned opposite said source and adapted for passing the bulk material between said at least one detector and said source;
a gamma attenuation library including a plurality of coefficients; and
a processor in communication with said at least one detector, said processor programmed to execute a process for determining at least one absolute weight/impurity/component value from an output of said at least one detector.

14. The apparatus of claim 13 further including a sample analysis producing at least one coefficient, said at least one coefficient determined by comparing a plurality of results from a test of at least one sample of the bulk material with known constituents with a measurement of a spectrum of said at least one sample.

15. The apparatus of claim 13 wherein each of said plurality of coefficients is a measured spectrum of one of a pure element and a pure compound.

16. The apparatus of claim 13 wherein each of said plurality of coefficients is a curve of mass attenuation coefficients based on a measured spectrum of a pure element.

17. A computer system for measuring an absolute value of at least one component of a bulk material, comprising:
a memory medium for storing program code and a set of computer data;
an input/output unit for communicating with at least one detector responsive to a range of energy levels encompassing at least three energy levels produced by a gamma radiation source; and
a processing unit programmed to execute a process including:
receiving a first data set representing a measured gamma spectrum of the bulk material, said first data set produced by said at least one detector,
receiving a second data set representing a gamma spectrum measured with the bulk material not in a detection path of said at least one detector,
combining said first data set and said second data set to produce an attenuation gamma spectrum;
performing a least squares fit of said attenuation gamma spectrum with a library having at least one library spectrum,
determining a set of relative values of the bulk material, and
determining a set of absolute values of the bulk material based on at least one coefficient determined from a sample analysis.

18. The system of claim 17 wherein said set of absolute values includes one of an absolute weight value, an absolute impurity value, and an absolute component value.

19. The system of claim 17 wherein said at least one library spectrum includes at least one curve of mass attenuation coefficients.

20. The system of claim 17 wherein said library includes a measured spectrum of one of a pure element and a pure compound.

21. The system of claim 17 wherein said at least one coefficient is determined by comparing at least one result of a test of at least one sample of the bulk material with a measurement of a spectrum of said at least one sample, said test identifying at least one constituent of the bulk material.

22. The system of claim 17 wherein said at least one coefficient is determined by a process including:
receiving a first sample data set from a test of at least one sample of the bulk material, said first sample data set identifying at least one constituent of the bulk material,
receiving a second sample data set from a measurement of said at least one sample of the bulk material by said at least one detector, and
calculating said at least one coefficient from said first sample data set and said sample second data set.

23. An apparatus for measuring an absolute value of at least one component of a bulk material, said apparatus comprising:
a means for obtaining a material spectrum over a range of energies;
a means for obtaining an empty spectrum over said range of energies;
a means for combining said material spectrum with said empty spectrum; and
a means for determining at least one absolute value of a constituent of the bulk material.

24. A method in a computer system for measuring an absolute value of at least one component of a bulk material, the method comprising:
a) providing for receiving a first data set representing a measured gamma spectrum of the bulk material, said first data set produced by at least one detector responsive to a range of energy levels encompassing at least three energy levels produced by a gamma radiation source;
b) providing for receiving a second data set representing a gamma spectrum measured with the bulk material not in a detection path of said at least one detector;
c) providing for combining said first data set and said second data set to produce an attenuation gamma spectrum;
d) providing for performing a least squares fit of said attenuation gamma spectrum with at least one library spectrum;
e) providing for determining a set of relative values of the bulk material, and
f) providing for determining a set of absolute values of the bulk material based on at least one coefficient determined from a sample analysis, whereby a determination of the quality and content of the bulk material is made for future processing of the bulk material.

25. The method of claim 24 wherein said set of absolute values includes one of an absolute weight value, an absolute impurity value, and an absolute component value.

26. The method of claim 24 wherein said at least one library spectrum includes at least one curve of mass attenuation coefficients.

27. The method of claim 24 wherein said library includes a measured spectrum of one of a pure element and a pure compound.

28. The method of claim 24 wherein said at least one coefficient is determined by comparing a plurality of results from a test of at least one sample of the bulk material with a measurement of a spectrum of said at least one sample, said test identifying at least one constituent of the bulk material.

29. The method of claim 24 wherein said at least one coefficient is determined by a process including:
   providing for receiving a first sample data set from a test of at least one sample of the bulk material, said first sample data set identifying at least one constituent of the bulk material,
   providing for receiving a second sample data set from a measurement of said at least one sample of the bulk material by said at least one detector, and
   providing for calculating said at least one coefficient from said first sample data set and said sample second data set.

30. Computer readable media tangibly embodying a program of instructions executable by a computer to perform a method of measuring an absolute value of at least one component of a bulk material, said method comprising:
   a) providing for receiving a first data set representing a measured gamma spectrum of the bulk material, said first data set produced by at least one detector responsive to a range of energy levels encompassing at least three energy levels produced by a gamma radiation source;
   b) providing for receiving a second data set representing a gamma spectrum measured with the bulk material not in a detection path of said at least one detector;
   c) providing for combining said first data set and said second data set to produce an attenuation gamma spectrum;
   d) providing for performing a least squares fit of said attenuation gamma spectrum with a library having at least one library spectrum;
   e) providing for determining a set of relative values of the bulk material, and
   f) providing for determining a set of absolute values of the bulk material based on at least one coefficient determined from a sample analysis.

31. The media of claim 30 wherein said set of absolute values includes one of an absolute weight value, an absolute impurity value, and an absolute component value.

32. The media of claim 30 wherein said at least one library spectrum includes at least one curve of mass attenuation coefficients.

33. The media of claim 30 wherein said library includes a measured spectrum of one of a pure element and a pure compound.

34. The media of claim 30 wherein said at least one coefficient is determined by comparing a plurality of results from a test of at least one sample of the bulk material with known constituents with a measurement of a spectrum of said at least one sample.

35. The media of claim 30 wherein said at least one coefficient is determined by a process including:
   providing for receiving a first sample data set from a test of at least one sample of the bulk material, said first sample data set identifying at least one constituent of the bulk material,
   providing for receiving a second sample data set from a measurement of said at least one sample of the bulk material by said at least one detector, and
   providing for calculating said at least one coefficient from said first sample data set and said sample second data set.

36. A method for measuring an absolute value of at least one component of a bulk material, the method comprising the steps of:
   a) applying a gamma radiation having at least three energy levels to an empty bulk material handling system;
   b) detecting said gamma radiation as an empty spectrum covering a range of energy levels encompassing said at least three energy levels;
   c) applying said gamma radiation to the bulk material;
   d) detecting said gamma radiation as a material spectrum after said radiation passes through the bulk material, said material spectrum covering said range of energy levels encompassing said at least three energy levels;
   e) combining said empty spectrum and said material spectrum to obtain an attenuation gamma spectrum;
   f) matching said attenuation gamma spectrum to a library of spectra to produce a set of relative values; and
   g) determining a set of absolute values from said set of relative values, whereby a determination of the quality and content of the bulk material is made for future processing of the bulk material.

37. The method of claim 36 wherein said step f) of matching includes performing a least squares fit of said attenuation gamma spectrum with said library.

38. The method of claim 36 wherein said step g) of determining said set of absolute values includes determining at least one coefficient from a sample analysis, said sample analysis includes performing at least one test of at least one sample of the bulk material and obtaining a measurement spectrum of said at least one sample, said at least one coefficient determined by comparing a result of said at least one test with said measurement spectrum.

39. The method of claim 36 wherein said step g) of determining said set of absolute values includes determining at least one coefficient, said at least one coefficient determined by a process including:
   performing a test of at least one sample of the bulk material, said test identifying at least one constituent of the bulk material;
   measuring a sample spectrum of said at least one sample of the bulk material by said at least one detector; and
   calculating said at least one coefficient from said test and said sample spectrum.

40. The method of claim 36 wherein said library is compiled by performing the steps of:
   measuring a spectrum of one of a pure compound and a pure element; and
   determining at least one curve of mass attenuation coefficients.

41. The method of claim 36 wherein said library includes at least one curve of mass attenuation coefficients.

42. The method of claim 36 wherein said library includes a measured spectrum of one of a pure element and a pure compound.

43. The method of claim 36 wherein said set of absolute values includes one of an absolute weight value, an absolute impurity value, and an absolute component value.

* * * * *